(12) United States Patent
Awad et al.

(10) Patent No.: US 10,184,033 B1
(45) Date of Patent: Jan. 22, 2019

(54) SYNTHESIS OF SILVER-PMMA NANOCOMPOSITE FILM

(71) Applicant: KING SAUD UNIVERSITY, RIYADH (SA)

(72) Inventors: Manal Ahmed Gasmelseed Awad, Riyadh (SA); Awatif Ahmed Hendi, Riyadh (SA); Khalid Mustafa Osman Ortashi, Riyadh (SA); Amnah Bader Alanazi, Riyadh (SA); Batool Ali Marzouq Alzhrani, Riyadh (SA); Dina Wafiq Awad Soliman, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 15/957,666

(22) Filed: Apr. 19, 2018

(51) Int. Cl.
| | |
|---|---|
| *A01N 25/10* | (2006.01) |
| *A01N 59/16* | (2006.01) |
| *C02F 1/50* | (2006.01) |
| *C08J 5/18* | (2006.01) |
| *C08K 3/08* | (2006.01) |

(52) U.S. Cl.
CPC ............... *C08J 5/18* (2013.01); *A01N 25/10* (2013.01); *A01N 59/16* (2013.01); *C08K 3/08* (2013.01); *C02F 1/505* (2013.01); *C02F 2303/04* (2013.01); *C02F 2305/08* (2013.01); *C08J 2333/12* (2013.01); *C08K 2003/0806* (2013.01)

(58) Field of Classification Search
CPC ......... C08J 5/18; C08J 2333/12; A01N 59/16; A01N 25/10; C02F 1/505; C02F 2303/04; C02F 2305/08; C08K 3/08; C08K 2003/0806; B22F 1/0018; B22F 1/0044; B22F 1/0062; B22F 9/24
See application file for complete search history.

(56) References Cited

U.S. PATENT DOCUMENTS

| | | | |
|---|---|---|---|
| 9,428,399 | B1 | 8/2016 | Awad et al. |
| 2017/0100338 | A1 | 4/2017 | Awad et al. |

FOREIGN PATENT DOCUMENTS

| | | |
|---|---|---|
| CN | 101670013 A | 3/2010 |
| KR | 10-0747415 B1 | 8/2007 |

OTHER PUBLICATIONS

Alshareah, E. H., "Polystyrene-Poly(methyl methacrylate) Silver Nanocomposites: Significant Modification of the Thermal and Electrical Properties by Microwave Irradiation," Materials, (Jun. 13, 2016), 9, 458, pp. 1-17.*

(Continued)

*Primary Examiner* — Lucas A Stelling
(74) *Attorney, Agent, or Firm* — Richard C. Litman

(57) ABSTRACT

The synthesis of a silver-PMMA nanocomposite film includes mixing an aqueous extract of *Trigonella foenum-graecum* (also known as *Helba* and fenugreek) seeds with an aqueous solution of silver nitrate, thereby reducing the silver ions to silver metal nanoparticles. A solution of the silver nanoparticles is added to a solution of PMMA [poly (methyl methacrylate)] in N'N-dimethylformamide (DMF) with stirring at 90° C. A light brown solution of silver colloids develops, which is cast in a glass plate and the DMF is evaporated at room temperature, leaving a silver-PMMA nanocomposite film. Testing on water shows the silver-PMMA nanocomposite film prevents or inhibits growth of microbes, suggesting use as an antimicrobial or antibacterial agent, e.g., in water purification.

2 Claims, 5 Drawing Sheets

(56) References Cited

OTHER PUBLICATIONS

Pooloth, "Biosynthesis of Silver Nanoparticles using Trigonella Foenum Graecum and the Determination of their Antimicrobial Activity," International Journal of Science and Research (IJSR), vol. 2, Issue 5, May 2013.
Angelina et al., "Green Synthesis and Characterization of Silver Nanoparticles using Fenugreek Seed Extract," International Journal of Scientific and Research Publications, vol. 3, Issue 7, Jul. 2013.
Awad, M.A. et al., "Green Synthesis, Characterization, and Antibacterial Activity of Silver/Polystyrene Nanocomposite", Journal of Nanomaterials, Journal of Nanomaterials, Article ID 943821, pp. 1-6; Hindawi Publishing Corp. Jul. 22, 2015.
Singho, N.D., "Enhancement of the Refractive Index of Silver Nanoparticles in Poly (Methyl Methacrylate)", Inter. J. of Research in Engineering and Technology (IJRET) vol. 1, No. 4, pp. 231-234, 2012.

\* cited by examiner

SYNTHESIS OF SILVER-PMMA NANOCOMPOSITE FILM

BACKGROUND

1. Field

The disclosure of the present patent application relates to polymer/metal nanoparticle composites, and particularly to the synthesis of a silver-PMMA nanocomposite film wherein the silver nanoparticles are synthesized using green chemistry, the resulting nanocomposite having antibacterial properties suitable for water purification and other applications.

2. Description of the Related Art

Nanomaterials are some of the most studied materials of the past century, giving birth to a new branch of science known as "nanotechnology." Nanomaterials can be prepared from bulk amounts of material, but the small size and shape of the resulting nanoparticles is an entirely different chemical action profile compared to the "parent" bulk material.

The much smaller size of nanomaterials helps them to penetrate particular cellular sites, while their additional surface area facilitates increased adsorption and targeted delivery of the substance. Nanomaterials frequently are found to exist in volcanic dust, mineral composites, and in anthropogenic waste materials, such as coal combustion, diesel exhaust, and welding fumes. Engineered nanomaterials manufactured with nanoscale dimensions are generally grouped into distinct types, including carbon, metals, metal oxides, dendrimers and composites.

Silver nanoparticles (AgNPs) have been shown to form composites with polymers, such as polyvinyl alcohol, polypyrrole, polyvinylidene fluoride, chitosan, and cellulose. The formation of polymer-silver nanocomposites requires that the size of the nanoparticles in the polymer matrix be controllable, and that their distribution within the polymer matrix be uniform.

Nanomaterials can be synthesized by different methods, including chemical, physical, and biological methods. Some chemical and physical methods have resulted in or contributed to environmental contamination, since the chemical procedures involved can generate a large amount of hazardous byproducts. Thus, there is a need to continue to develop new "green" synthesis procedures for nanoparticles that are clean, safe, ecofriendly, and nontoxic, without the use of high pressure, energy, temperature, and toxic chemicals. The biological methods include synthesis of nanomaterials from the extracts of plant, bacterial, and fungal species, among other procedures.

Thus, the synthesis of a silver-PMMA nanocomposite film solving the aforementioned problems is desired.

SUMMARY

The synthesis of a silver-PMMA nanocomposite film includes mixing an aqueous extract of *Trigonella foenum-graecum* (also known as *Helba* and fenugreek) seeds with an aqueous solution of silver nitrate, thereby reducing the silver ions to silver metal nanoparticles. A solution of the silver nanoparticles is added to a solution of PMMA [poly (methyl methacrylate)] in N'N-dimethylformamide (DMF) with stirring at 90° C. A light brown solution of silver colloids develops, which is cast in a glass plate and the DMF is evaporated at room temperature, leaving a silver-PMMA nanocomposite film. Testing on water shows the silver-PMMA nanocomposite film prevents or inhibits growth of microbes, suggesting use as an antimicrobial or antibacterial agent, e.g., in water purification.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
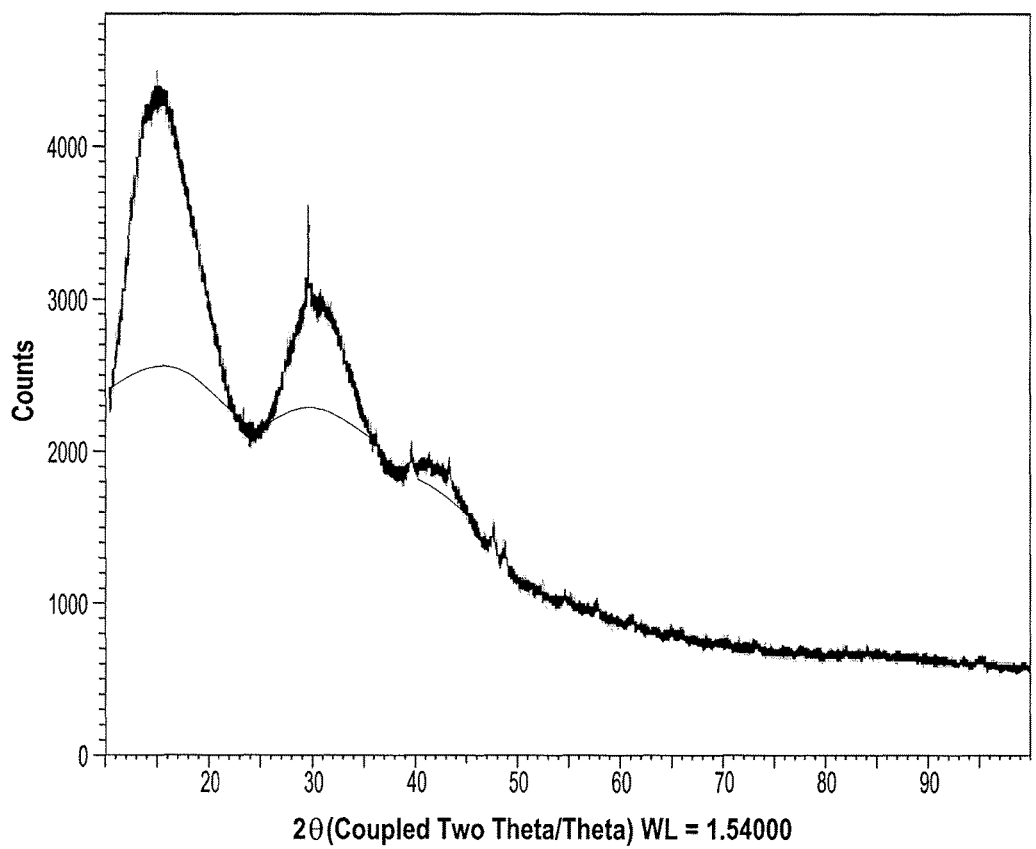
FIG. 1A is an X-ray powder diffraction (XRD) plot of pure PMMA [poly (methyl methacrylate)] polymer.

The synthesis of a silver-PMMA nanocomposite film using *Trigonella foenum-graecum* aqueous extract to synthesize the silver nanoparticles and subsequent synthesis of the polymer nanocomposite film, and analysis of the antimicrobial activity of the nanocomposite, is set forth below.

Seeds from fenugreek, or *Helba* (*Trigonella foenum-graecum*) are washed and dried, and then soaked in boiled distilled water overnight. The aqueous extract is then filtered, and combined filtrates are used as a precursor for preparing the nanoparticles.

The nanoparticles are prepared by treating the combined filtrates with an aqueous solution of silver nitrate ($AgNO_3$). The aqueous silver nitrate solution is first formed by dissolving silver nitrate in distilled water, with vigorous stirring and at 80° C., for 5 minutes. The extract is then added to the silver nitrate solution, and the nanoparticle solution is incubated at room temperature until it is used.

To form the nanocomposite film, PMMA is dissolved in DMF (dimethyl formamide), and then the silver nanoparticle solution is added, and stirred for one hour. The resulting solution is cast on a glass plate. The DMF is allowed to evaporate at room temperature, resulting in the nanocomposite film. Once dried, the nanocomposite film is removed from the glass plate.

The nanocomposite film demonstrates higher thermal stability than pure PMMA. The nanocomposite also demonstrates substantial antibacterial activity, as measured by comparing tap water treated with the nanocomposite material with untreated tap water.

Example 1

Preparation of Greener *Helba* AgNPs/PMMA Nanocomposite Film

We obtained *Trigonella foenum-graecum* (*Helba*) seeds from a local market in Saudi Arabia. We washed and dried 3 g of the seeds, and then soaked them in 90 ml of boiled, distilled water overnight, to prepare a *Helba* extract. The *Helba* extract was filtered, and the filtrate was immediately used for preparation of the nanoparticles solution. The filtrate was treated with an aqueous solution of silver nitrate ($AgNO_3$), which was first prepared as follows.

We dissolved 1 mmol/ml of silver nitrate ($AgNO_3$, analytical grade, obtained from Techno Pharmchem, India) in 50 ml of distilled water, with vigorous stirring at 80° C. for 5 minutes. Then the *Helba* extract filtrate was added to the silver nitrate solution. The colloidal solution changed in color from colorless to brown, as noted by visual observation, confirming reduction of the silver ions and the formation of the greener AgNPs. Then, the resulting nanoparticle solution was incubated at room temperature until it was used.

We obtained PMMA from SABIC Company, in Saudi Arabia. We dissolved 6 g of the PMMA in dimethylformamide (DMF) obtained from R & M Marketing, in Essex, UK. A freshly prepared solution of the greener silver nanoparticles was added to the PMMA solution. The addition was carried out in a hood under constant stirring at 90° C. The mixture was stirred for 1 hour in order to complete the reaction.

The resulting solution was light brown, due to the formation of silver colloids. The solution was then cast on a glass plate. The DMF was evaporated at room temperature, resulting in the nanocomposite film. Once dry, the film was removed from the glass plate.

Figure 1B:
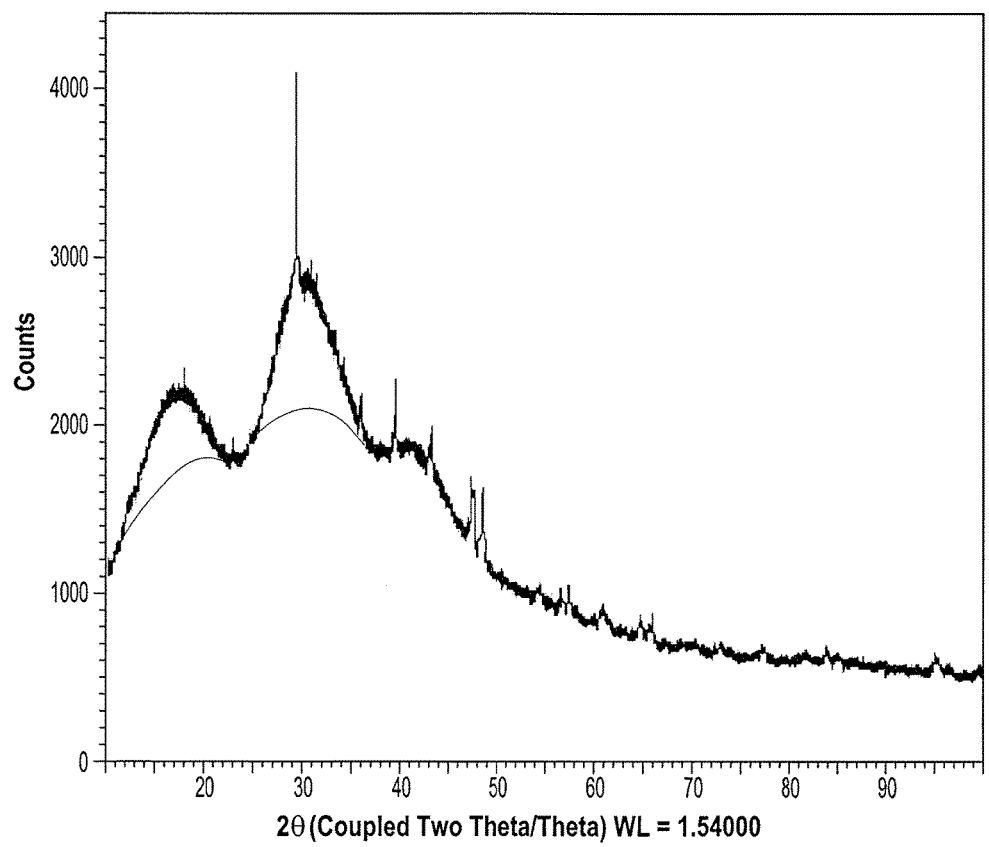
FIG. 1B is an XRD plot of a silver-PMMA nanocomposite film synthesized as described herein.
Figure 4A:
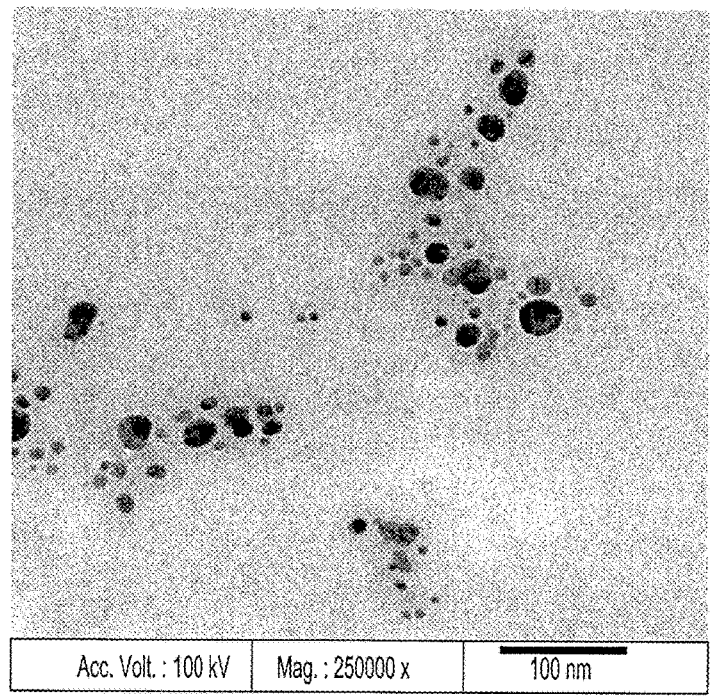
FIG. 4A is a TEM (transmission electron microscopy) micrograph of silver nanoparticles prepared using *Helba* extract, the scale bar corresponding to 100 nm.
Figure 4B:
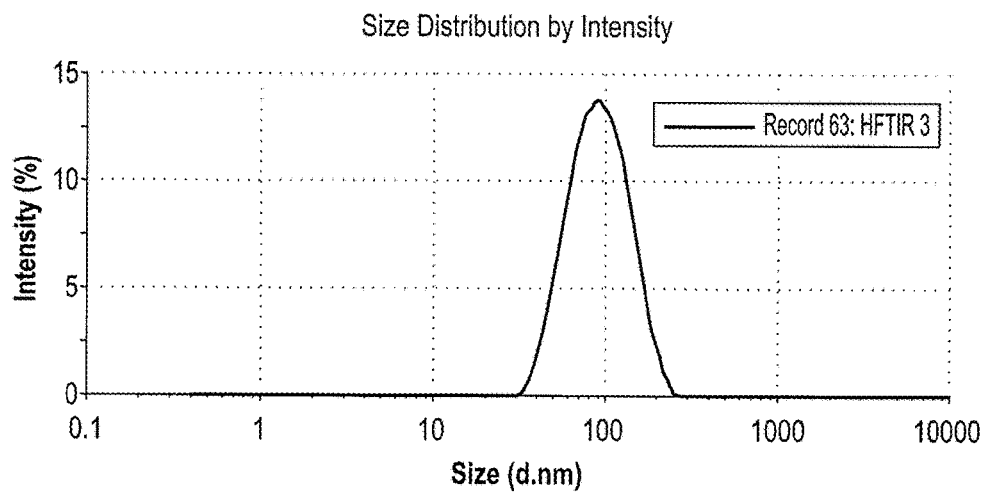
FIG. 4B shows the size distribution curve of the silver nanoparticles prepared using *Helba* extract, determined by DLS (dynamic light scattering), the average size being 83.01 nm.

We used transmission electron microscopy (TEM) using a JEM-1011 transmission electron microscope, obtained from JEOL, in Japan, to characterize the size, shape, and morphology of the synthesized nanoparticles, using accelerating voltage of 100 KV. See FIG. 4A. X-ray diffraction (XRD) was performed on a Bruker D8 Discover, to examine and compare the greener AgNPs/PMMA nanocomposite and PMMA films. See FIGS. 1A and 1B. The average particle size of the silver nanoparticles was estimated to be 83.01 nm.

TGA (thermogravimetric analysis) thermograms were carried out on a Mettler Toledo TGA/DSC 1, providing comparison between the greener AgNPs/PMMA nanocomposite and PMMA films. See FIG. 2. About 4 mg of dried film in each sample was used for the TGA comparison. TGA thermograms were obtained through a range of 0-800° C., under nitrogen air flow, at a rate of 10° C./min. The distinct graphs were plotted with weight (percentage) loss against temperature.

Example 2

Microbiological Testing

To treat the tap water with the greener nanocomposite film, a 1×1 cm square of the film was soaked in 50 ml tap water in a glass Erlenmeyer flask for 48 hours. Then, the treated water was tested for microorganism activity.

To prepare 250 ml general purpose nutrient agar medium, we dissolved 7 g of the agar medium in 250 ml of distilled water. To prepare 250 ml Eosin methylene blue (EMB) agar medium for the isolation of coliforms and *E. coli*, we dissolved 12.87 g of the agar medium in 250 ml of distilled water. For Mueller Hinton agar (MHA) medium, we dissolved 9.5 g of the agar medium in 250 ml of distilled water. Each of these was subsequently autoclaved, and, for testing, we added 100 µl tap water (untreated or treated), mixed thoroughly, and poured each medium mixture into a petri dish. The plates were then incubated at 37° C. for 24-48 hours.

Figure 3:
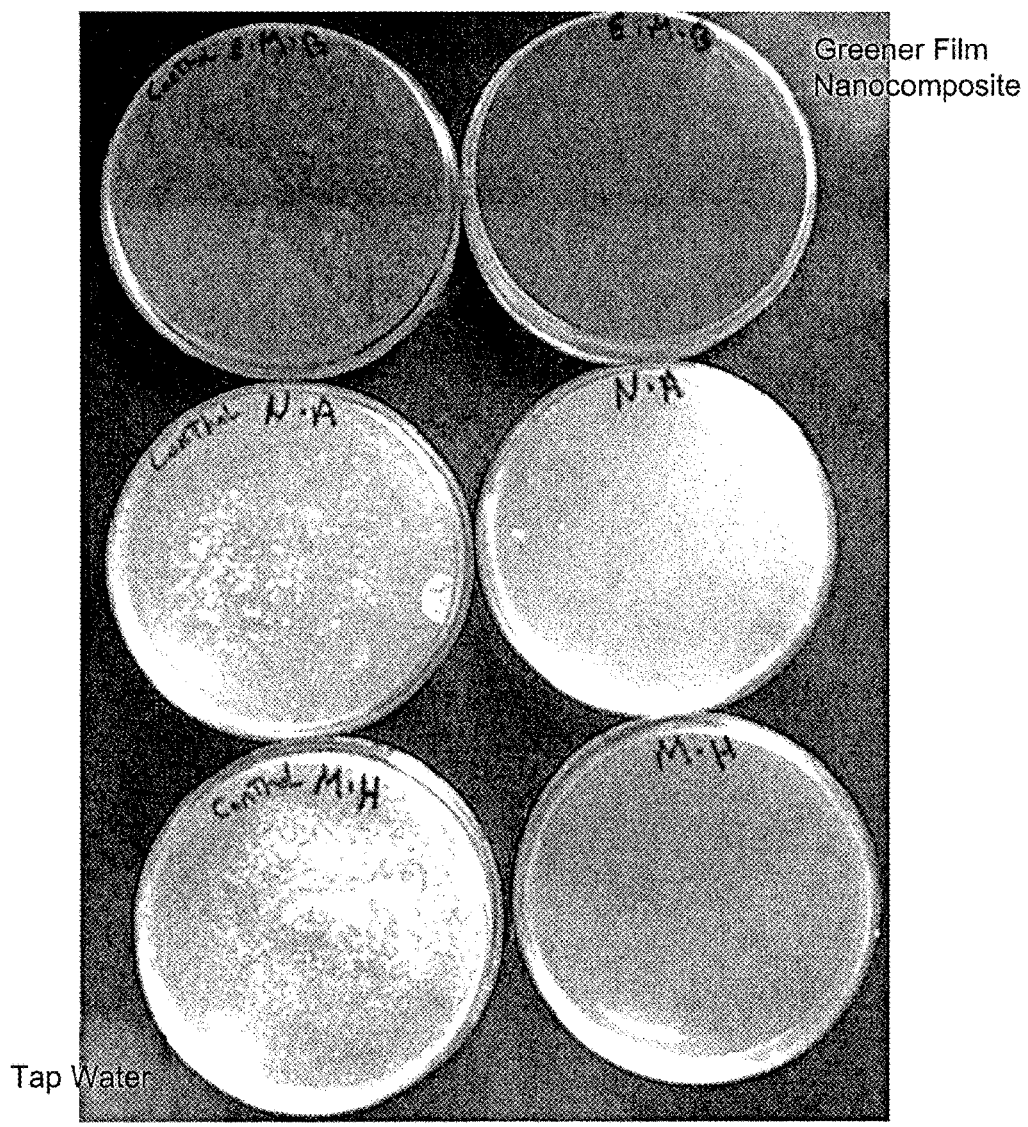
FIG. 3 is a photograph of plated microorganism activity assays comparing treated and untreated tap water samples.

In each instance, the treated sample exhibited no microorganism growth, in stark contrast to the tap water control. See FIG. 3.

Figure 2:
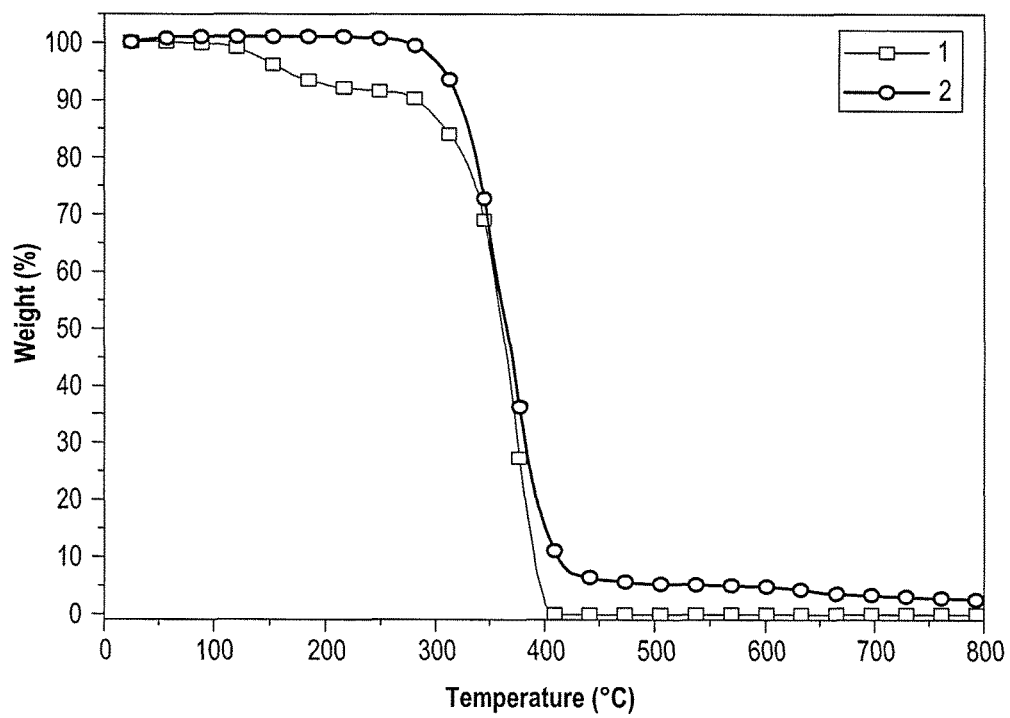
FIG. 2 is a composite plot of TGA (thermogravimetric analysis) thermograms for pure PMMA polymer (line 1) and a silver-PMMA nanocomposite film synthesized as described herein (line 2).

As noted above, TGA was performed comparing the AgNPs/PMMA nanocomposites and pure PMMA. See FIG. 2. The weighed samples were heated at a rate of 10° C./min, from room temperature to 800° C., which is in the middle of the boiling point of the solvent and the degradation temperature of the polymer. FIG. 2 demonstrates two particular phases over the temperature range. The underlying weight reduction was figured to be around 20% and 5% for PMMA and Ag/PMMA, respectively, for the range of room temperature up to 300° C. The weight reduction for this range of temperature is credited to low sub-atomic weight oligomers, loss of dampness, and leftover dissolvables in this scope of temperatures.

The second weight reduction demonstrates the corruption at over 360° C. of the pure PMMA, which totally disintegrates at 400° C., while the Ag/PMMA nanocomposite portion disintegrates over 800° C. This second significant weight reduction was ascribed to basic deterioration of the polymer.

The weight reduction of Ag/PMMA nanoparticles and pure PMMA is organized in FIG. 2. The TGA investigation of Ag/PMMA nanocomposite indicates a decomposition profile beginning at 400° C. and proceeding until over 800° C. This demonstrates that the high thermal stability of the polymer is enhanced because of the presence of Ag as a nano-filler.

Thus, the greener *Helba* AgNPs/PMMA nanocomposite demonstrates higher thermal stability than the PMMA polymer alone, along with significant antibacterial activity. There was no visible growth of microbes in the treated water samples. Thus, these AgNPs provide a promising potential use in water purification, water containers, filters, water and wastewater treatment, and various associated industrial and commercial applications.

It is to be understood that the synthesis of a silver-PMMA nanocomposite film is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for synthesis of a silver-PMMA nanocomposite film, comprising the steps of:
    dissolving silver nitrate in distilled water at 80° C. under continuous stirring to obtain an aqueous solution of silver ions;
    extracting seeds of *Trigonella foenum-graecum* in water to obtain an aqueous *Trigonella* extract, wherein the step of extracting seeds of *Trigonella foenum-graecum* comprises the steps of:
        i) washing and drying the seeds;
        ii) soaking the seeds in boiled distilled water overnight to obtain a crude extract; and
        iii) filtering the crude extract and retaining the filtrate as the aqueous *Trigonella* extract;
    mixing the aqueous solution of silver ions with the aqueous *Trigonella* extract to obtain silver nanoparticles in water, wherein the silver nanoparticles have an average size of 83.01 nm;

mixing the silver nanoparticles in water with poly (methyl methacrylate) [PMMA] in an organic solvent at 90° C. to obtain a colloidal solution of a nanocomposite of silver nanoparticles and PMMA;

casting the colloidal solution on a support; and evaporating the organic solvent at room temperature to obtain a silver-PMMA nanocomposite film.

2. The method for synthesis of a silver-PMMA nanocomposite film according to claim 1, wherein the organic solvent comprises N',N-dimethylformamide (DMF).

* * * * *